(12) United States Patent
Kastelein et al.

(10) Patent No.: US 7,427,402 B2
(45) Date of Patent: Sep. 23, 2008

(54) METHOD OF EVALUATING INFLAMMATORY SKIN DISORDERS USING IL-17 AND/OR IL-19

(75) Inventors: Robert A. Kastelein, Redwood City, CA (US); Terrill K. McClanahan, Sunnyvale, CA (US); Erin Murphy, Mountain View, CA (US); Jason R. Chan, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/635,960

(22) Filed: Dec. 8, 2006

(65) Prior Publication Data

US 2007/0098727 A1 May 3, 2007

Related U.S. Application Data

(63) Continuation of application No. 11/218,446, filed on Sep. 2, 2005, now abandoned, which is a continuation-in-part of application No. 11/120,518, filed on May 2, 2005.

(60) Provisional application No. 60/567,747, filed on May 3, 2004.

(51) Int. Cl.
*A61K 39/00* (2006.01)
*A61K 45/00* (2006.01)
*A61K 31/70* (2006.01)
*C12Q 1/00* (2006.01)
*C12Q 1/68* (2006.01)

(52) U.S. Cl. ............... 424/145.1; 424/85.1; 424/85.2; 424/184.1; 435/4; 435/6; 514/44

(58) Field of Classification Search .............. None
See application file for complete search history.

(56) References Cited

U.S. PATENT DOCUMENTS

| 7,090,847 B1 | 8/2006 | Oppmann et al. |
| 7,183,057 B2 | 2/2007 | Benson |
| 2003/0083231 A1 | 5/2003 | Ahlem et al. |

FOREIGN PATENT DOCUMENTS

| WO | WO 99/60127 | 11/1999 |
| WO | WO 00/55204 | 9/2000 |
| WO | WO 01/46420 | 6/2001 |
| WO | WO 01/85790 | 11/2001 |
| WO | WO 02/078729 | 10/2002 |
| WO | WO 02/102411 | 12/2002 |
| WO | WO 2004/042009 | 5/2004 |
| WO | WO 2004/060291 | 7/2004 |
| WO | WO 2005/010044 | 2/2005 |

OTHER PUBLICATIONS

Teunissen et al., J Invest Dermatol Oct. 1998; 111(4):645-649.*
Kurasawa et al., Arth & Rheum Nov. 2000 43(11):2455-2463.*
Romer et al., J Invest Derm Dec. 2003 121(6):1306-1311.*
Griffiths et al., Br J Dermatol Jun. 1991; 124(6):519-26.*
Aggarwal and Gurney (2002) *J. Leukocyte Biology* 71:1-8 "IL-17: prototype member of an emerging cytokine family".
Aggarwal et al. (2003) *J. Biol. Chem.* 278:1910-1914 Interleukin-23 Promotes a Distance CD4 T Cell Activation State Characterized by the Production of Interleukin-17.
Blumberg et al. (2001) *Cell* 104:9-19 "Interleukin 20: Discovery, Receptor Identification, and Role in Epidermal Function".
Fossiez et al. (1996) *J. Exp. Med.* 183:2593-2603 "T Cell Interleukin-17 Induces Stromal Cells to Produce Proinflammatory and Hamatopoietic Cytokines".
Ghoreschi et al. (2003) *Nat Med* 9:40-46 "Interleukin-4 threapy of psoriasis Th2 responses and improves human autoimmune disease".
Griffiths et al. (1991) *Br J Dermatol.* 124(6):519-526 "Modulation of leucocyte adhesion molecules, a T-cell chemotaxin (IL-8) and a regulatory cytokine (TNF-α) in allergic contact dermatitis (*Rhus dermatitis*)".
Gudjonsson et al. (2004) *Clin Exp Immunol.* 135(1):1-8, Review "Immunopathogenic mechanisms in psoriasis".
Kawaguchi et al. (2001) *J. Immunol.* 167:4430-4435 "Identification of a Novel Cytokine, ML-1, and Its Expression in Subjects with Asthma".
Kawaguchi et al. (2004) *J. Allergy Clin. Immunol.* 114:1265-1273 "IL-17 cytokine family".
Kennedy et al. (1996) *J. Interferon Cytokine Res.* 16:611-617 "Mouse IL-17: a cytokine preferntially expressed by alpha beta TCR+CD4- CD8-T cells".
Kurasawa et al. (2000) *Arth & Rheum.* 43(11):2455-2463 "Increased Interleukin-17 Production in Patients with Systemic Sclerosis".
Lee et al. (2004) *J Exp Med* 199:125-130 "Increased Expression of Interleukin 23 p19 and p40 in Lesional Skin of Patients with Psoriasis vularis".

(Continued)

*Primary Examiner*—Gary Nickol
*Assistant Examiner*—Cherie M Woodward
(74) *Attorney, Agent, or Firm*—Schering-Plough Patent Department

(57) ABSTRACT

Provided are methods for diagnosing the propensity of a subject to develop skin inflammation, in particular, psoriasis. Also provided are methods of treatment with antagonists of IL-17, IL-19, and/or IL-23.

12 Claims, No Drawings

OTHER PUBLICATIONS

Liao et al. (2002) *J Immunol* 169:4288-4297 "IL-19 Induces Production of IL-6 and TNF-α".

Liao et al. (2004) *J Immunol.* 173:6712-6718 "IL-19 Induced Th2 Cytokines and Was Up-Regulated in Asthma Patients".

Nagalakshmi et al. (2004) *Int Immunopharmacol* 4:577-592 "Expression patterns of IL-10 ligand and receptor gene families provide leads for biological characterization".

Oppmann et al. (2000) *Immunity* 13:715-725 "Novel p19 Protein Engages Il-12p40 to From a Cytokine, IL-23, with Biological Activities Similar as Well as Distinct from IL-12".

Parrish-Novak (2002), *J Biol Chem* 277: 47517-47523 "Interleukins 19, 20, and 24 Signal through Two Distinct Receptor Complexes".

Romer et al. (2003) *J Invest Dermatol* 6:1306-1311 "Epidermal Overexpression of Interleukin-19 and -20 mRNA in Psoriatic Skin Disappears After Short-Term Treatment with Cyclosporine A or Calcipotriol", Rouvier et al. (1993) *J. Immunol.* 150:5445-5456 "CTLA-8, Clones from an Activated T Cell, Bearing AU-Rich Messenger RNA Instability Sequences, and Homologous to a Herpesvirus Saimiri Gene".

Starnes et al. (2001) *J. Immunol.* 167:4137-4140 "Cutting Edge: IL-17F, a Novel Cytokine Slectively Expressed in Activated T Cells and Monocytes, Regulates Angiogenesis and Endothelial Cell Cytokine Production".

Teunissen et al. (1998) *J. Invest. Derm.* 111(4):645-649. Review "Interleukin0-17 and interferon-gamma synergize in the enhancement of proinflammatory cytokine production by human keratinocytes".

Witowski et al. (2004) *Cellular and Molecular Life Sciences* 61(5):567-579 "Interleukin-17: a mediator of inflammatory respones".

Wang et al. (2002) *J. Biol Chem* 277:7341-7347 "Interleukin 24 (MDA-7/MOB-5) Signals through Two Heterodimeric Receptors, IL-22R1/IL-20R2 and IL-20R1/IL-20R2".

Wiekowski et al. (2001) *J. Immunol.* 166:7563-7570 "Ubiquitous Transgenic Expression of the Il-23 Subunit p19 Induces Multiorgan Inflammation, Runting, Infertility, and Premature Death".

Yao et al. (1995) *Immunity* 3:811-821 "Herpesvirus Saimiri Encodes a New Cytokine, IL-17, Which Binds to a Novel Cytokine Receptor".

\* cited by examiner

SEQUENCE LISTING

<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: PCR forward primer for human IL-17A -continued

```
<400> SEQUENCE: 1
caaccgatcc acctcacctt                                              20

<210> SEQ ID NO 2
<211> LENGTH: 19
<212> TYPE: DNA
<213> ORGANISM: Artificial
<220> FEATURE:
<223> OTHER INFORMATION: PCR Reverse primer for human IL-17A

<400> SEQUENCE: 2
ggcactttgc ctcccagat                                               19

<210> SEQ ID NO 3
<211> LENGTH: 23
<212> TYPE: DNA
<213> ORGANISM: Artificial
<220> FEATURE:
<223> OTHER INFORMATION: PCR Forward primer for human IL-17F

<400> SEQUENCE: 3
tgccaggagg tagtatgaag ctt                                          23

<210> SEQ ID NO 4
<211> LENGTH: 22
<212> TYPE: DNA
<213> ORGANISM: Artificial
<220> FEATURE:
<223> OTHER INFORMATION: PCR Reverse primer for human IL-17F

<400> SEQUENCE: 4
atgcagccca agttcctaca ct                                           22

<210> SEQ ID NO 5
<211> LENGTH: 22
<212> TYPE: DNA
<213> ORGANISM: Artificial
<220> FEATURE:
<223> OTHER INFORMATION: PCR Forward Primer for human IL-19

<400> SEQUENCE: 5
ttggctcctg ggtacaatac tg                                           22

<210> SEQ ID NO 6
<211> LENGTH: 22
<212> TYPE: DNA
<213> ORGANISM: Artificial
<220> FEATURE:
<223> OTHER INFORMATION: PCR Reverse Primer for human IL-19

<400> SEQUENCE: 6
tccttagctt ggatggctct tt                                           22
```

METHOD OF EVALUATING INFLAMMATORY SKIN DISORDERS USING IL-17 AND/OR IL-19

This application is a Continuation application of U.S. patent application Ser. No. 11/218,446, filed Sep. 2, 2005 now abandoned, which is a Continuation-In-Part application of U.S. patent application Ser. No. 11/120,518, filed May 2, 2005, which claims benefit from U.S. Provisional Patent Application No. 60/567,747, filed May 3, 2004.

FIELD OF THE INVENTION

The present invention relates to methods of analysis the propensity to develop skin inflammatory disorders, in particular, psoriasis. Also provided is a method of treatment to prevent such skin inflammatory disorders using antagonists of IL-17A, IL-17F, IL-19, and/or IL-23.

BACKGROUND OF THE INVENTION

The skin serves as an important boundary between the internal milieu and the environment, preventing contact with potentially harmful antigens. In the case of antigen/pathogen penetration, an inflammatory response is induced to eliminate the antigen. This response leads to a dermal infiltrate that consists predominantly of T cells, polymophonuclear cells, and macrophages (see, e.g., Williams and Kupper (1996) *Life Sci.*, 58:1485-1507.) Normally, this inflammatory response, triggered by the pathogen, is under tight control and will be halted upon elimination of the pathogen.

In certain cases, this inflammatory response occurs without external stimuli and without proper controls, leading to cutaneous inflammation. Cutaneous inflammation, the result of the cellular infiltrate noted above as well as the secreted cytokines from these cells, encompasses several inflammatory disorders such as cicatricial pemphigoid, scleroderma, hidradenitis suppurativa, toxic epidermal necrolysis, acne, osteitis, graft vs. host disease (GvHD), pyoderma gangrenosum, and Behcet's Syndrome (see, e.g., Willams and Griffiths (2002) *Clin. Exp. Dermatol.*, 27:585-590). The most common form of cutaneous inflammation is psoriasis.

Psoriasis is characterized by T cell mediated hyperproliferation of keratinocytes coupled with an inflammatory infiltrate. The disease has certain distinct overlapping clinical phenotypes including chronic plaque lesions, skin eruptions, and pustular lesions (see, e.g., Gudjonsson, et al. (2004) *Clin Exp. Immunol.* 135:1-8). Approximately 10% of psoriasis patients develop arthritis. The disease has a strong but complex genetic predisposition, with 60% concordance in monozygotic twins.

The typical psoriatic lesion is a well defined erythematous plaque covered by thick, silvery scales. The inflammation and hyperproliferation of psoriatic tissue is associated with a different histological, antigenic, and cytokine profile than normal skin. Among the cytokines associated with psoriasis are: TNFα, IL-19, IL-18, IL-15, IL-12, IL-7, IFNγ, IL-17A and IL-23 (see, Gudjonsson, et al., supra). IL-17A has been detected in psoriatic skin.

To date, prediction of psoriasis flare-ups has been hampered by lack of knowledge of the cytokine changes between nonlesional and lesional psoriatic tissue. The present invention fills this unmet need by providing a method of comparing IL-17A, IL-17F, and IL-19 expression in nonlesional psoriatic skin relative to normal skin, thus affording the ability to assess probability of the formation of lesional psoriasis.

SUMMARY OF THE INVENTION

The invention is based, in part, upon the discovery that IL-17A, IL-17F (collectively, "IL-17"), and IL-19 mRNA levels are comparably elevated in non-lesional psoriatic tissue as compared to normal or non-psoriatic skin tissue.

The present invention provides a method of evaluating the propensity of a subject to develop an inflammatory skin disorder comprising: a) obtaining a sample of skin from the subject; and b) quantifying the level of IL-17 or IL-19 expression in the sample. In one embodiment, the IL-17 or IL-19 expression is mRNA expression, and level of IL-17 or IL-19 expression is quantified by real-time PCR.

The invention further provides that the inflammatory skin disorder is cutaneous inflammation, in particular, psoriasis. The skin sample can be from lesional or non-lesional psoriatic skin. In certain embodiments, the level of IL-17 expression in the skin sample is an average value between 5 and 20 fold higher in than normal skin. The average value for IL-19 expression can be between 5 and 130 fold higher than normal skin.

In a further embodiment, the skin sample is from non-lesional psoriatic skin. Also encompassed is that the non-lesional psoriatic skin sample is from a subject having: a) a family history of psoriasis; or b) previously presented psoriatic symptoms. In a further embodiment, subject is a human.

The present invention also provides a method of preventing skin inflammation comprising administering to a subject exhibiting a propensity to develop skin inflammation: a) an antagonist of IL-17; b) an antagonist of IL-23; c) an antagonist of IL-19; or d) an antagonist of at least two cytokines selected from the group consisting of IL-17, IL-19, or IL-23. In one embodiment the skin inflammation is cutaneous inflammation, in particular, psoriasis. In this method of preventing skin inflammation, subject expresses an average value of at least 5 fold higher IL-17 expression in a non-lesional psoriatic skin sample compared to a normal skin sample, as quantified by real-time PCR. The average value of IL-19 expression is at least 20 fold higher.

The invention further provides that the antagonist of IL-17, IL-19, and/or IL-23 is an: a) antibody or binding fragment thereof; b) siRNA; or c) a small molecule inhibitor. In a further embodiment, the antibody is: a) a polyclonal antibody; b) a monoclonal antibody; c) a humanized antibody; d) a bi-specific antibody.

DETAILED DESCRIPTION

As used herein, including the appended claims, the singular forms of words such as "a," "an," and "the" include their corresponding plural references unless the context clearly dictates otherwise. All references cited herein are incorporated by reference to the same extent as if each individual publication, patent application, or patent, was specifically and individually indicated to be incorporated by reference.

I. Definitions.

"Activity" of a molecule may describe or refer to binding of the molecule to a ligand or to a receptor, to catalytic activity, to the ability to stimulate gene expression, to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" may also mean specific activity, e.g., [catalytic activity]/[mg protein], or [immunological activity]/[mg protein], or the like.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. Treatment encompasses methods using a purified immune cell, e.g., in a mixed cell reactions or for administration to a research, animal, or human subject. The invention contemplates treatment with a cell, a purified cell, a stimulated cell, a cell population enriched in a particular cell, and a purified cell. Treatment further encompasses situations where an administered reagent or administered cell is modified by metabolism, degradation, or by conditions of storage.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, including selenomethionine, as well as those amino acids that are modified after incorporation into a polypeptide, e.g., hydroxyproline, O-phosphoserine, O-phosphotyrosine, gamma-carboxyglutamate, and cystine. Amino acid analogs refers to compounds that have the same basic chemical structure as a naturally occurring amino acid, i.e., an $\alpha$-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetic refers to a chemical compound that has a structure that is different from the general chemical structure of an amino acid, but that functions in a manner similar to a naturally occurring amino acid. Amino acids may be referred to herein by either their commonly known three letter symbols or by their one-letter symbols.

"Binding composition" refers to a molecule, small molecule, macromolecule, antibody, a fragment or analogue thereof, or soluble receptor, capable of binding to a target. "Binding composition" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. "Binding composition" may also refer to a molecule in combination with a stabilizer, excipient, salt, buffer, solvent, or additive, capable of binding to a target. "Binding" may be defined as an association of the binding composition with a target where the association results in reduction in the normal Brownian motion of the binding composition, in cases where the binding composition can be dissolved or suspended in solution.

"Bispecific antibody" generally refers to a covalent complex, but may refer to a stable non-covalent complex of binding fragments from two different antibodies, humanized binding fragments from two different antibodies, or peptide mimetics derived from binding fragments from two different antibodies. Each binding fragment recognizes a different target or epitope, e.g., a different receptor, e.g., an inhibiting receptor and an activating receptor. Bispecific antibodies normally exhibit specific binding to two different antigens.

"Cutaneous Inflammation" refers to improper regulation of the immune response in the skin or dermis, leading to an infiltrate of inflammatory cells and release of various inflammatory factors, including cytokines. Cutaneous inflammation includes psoriasis, atopic dermatitis, scleroderma, and the like.

Endpoints in activation or inhibition can be monitored as follows. Activation, inhibition, and response to treatment, e.g., of a cell, skin tissue, keratinocyte, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) Glia 36:235-243; Stanimirovic and Satoh (2000) *Brain Pathol.* 10:113-126).

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferabl "Exogenous" refers to substances that are produced outside an organism, cell, or human body, depending on the context. "Endogenous" refers to substances that are produced within a cell, organism, or human body, depending on the context.

"IL-17" as used herein, unless specifically stated otherwise, can mean IL-17A and/or IL-17F.

The "level of IL-17 expression" or "level of IL-19 expression" refers to real-time PCR values that are normalized to ubiquitin. Kruskal-Wallis statistical analysis is performed on log transformed data (median method). Typically the calculated average level of IL-17 mRNA expression in non-lesional psoriatic tissues is between 2 and 50 fold higher than normal tissues. Preferably the level is between 5 and 20 fold higher.

A "marker" relates to the phenotype of a cell, tissue, organ, animal, or human subject. Markers are used to detect cells, e.g., during cell purification, quantitation, migration, activation, maturation, or development, and may be used for both in vitro and in vivo studies. An activation marker is a marker that is associated with cell activation.

"Monofunctional reagent" refers, e.g., to an antibody, binding composition derived from the binding site of an antibody, an antibody mimetic, a soluble receptor, engineered, recombinant, or chemically modified derivatives thereof, that specifically bind to a single type of target. For example, a monofunctional reagent may contain one or more functioning binding sites for an IL-17, IL-19, or IL-23 ligand or receptor. "Monofunctional reagent" also refers to a polypeptide, antibody, or other reagent that contains one or more functioning binding sites for, e.g., IL-17, IL-19, or IL-23 ligand or receptor and one or more non-functioning binding sites for another type of receptor. For example, a monofunctional reagent may comprise an antibody binding site for IL-17, IL-19, or IL-23 ligand or receptor plus an Fc fragment that has been engineered so that the Fc fragment does not specifically bind to Fc receptor.

"Nucleic acid" refers to deoxyribonucleotides or ribonucleotides and polymers thereof in either single stranded or double-stranded form. The term nucleic acid may be used interchangeably with gene, cDNA, mRNA, oligonucleotide, and polynucleotide. A particular nucleic acid sequence also implicitly encompasses "allelic variants" and "splice variants."

"Condition" of skin encompasses disorders but also states that are not necessarily classified as disorders, e.g., cosmetic conditions or states of normal physiology. Disorders of a the skin encompass disorders of a cell, where the cell is in the same genetic lineage of the skin, e.g., a precursor cell of dermal keratinocytes where the precursor is committed to becoming a keratinocyte.

"Sample" refers to a sample from a human, animal, or to a research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

Small molecules are provided for the treatment of physiology and disorders of the skin, e.g., cutaneous inflammation. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecule toxins are described (see, e.g., U.S. Pat. No. 6,326,482 issued to Stewart, et al).

"Specifically" or "selectively" binds, when referring to a ligand/receptor, antibody/antigen, or other binding pair, indicates a binding reaction which is determinative of the presence of the protein in a heterogeneous population of proteins and other biologics. Under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity or binding constant that is at least two fold greater, preferably at least ten times greater, more preferably at least 20-times greater, and most preferably at least 100-times greater than the affinity with any other antibody, or binding composition derived thereof. In a preferred embodiment the antibody will have an affinity that is greater than about $10^9$ liters/mol, as determined, e.g., by Scatchard analysis (Munsen, et al. (1980) *Analyt. Biochem.* 107:220-239).

"Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of a IL-17 or IL-23 antagonist to a human or animal subject, or to a cell, tissue, physiological compartment, or physiological fluid. "Treatment of a cell, tissue, organ, or subject" encompasses situations where it has not been demonstrated that the antagonist of IL-17 or IL-23 has contacted their respective receptors, or a cell expressing these receptors.

"Therapeutically effective amount" of a therapeutic agent is defined as an amount of each active component of the pharmaceutical formulation that is sufficient to show a meaningful patient benefit, i.e., to cause a decrease in, amelioration of, or prevention of the symptoms of the condition being treated. When the pharmaceutical formulation comprises a diagnostic agent, "a therapeutically effective amount" is defined as an amount that is sufficient to produce a signal, image, or other diagnostic parameter that facilitates diagnosis. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530).

II. General.

Mammalian skin consists of dermal (inner) and epidermal (outer) layers. The epidermis is made almost entirely of keratinocytes (95%) with other cell types including Langerhans cells and melanocytes. The epidermis is rapidly growing, turning over every seven days in the mouse. In psoriasis, this turnover is shortened to 3-5 days as a result of keratinocyte hyperproliferation.

The present invention is based, in part, upon the discovery that non-lesional psoriatic tissues expresses IL-17A mRNA at significantly elevated levels when compared to normal or non-psoriatic tissue. A human inflammatory skin panel was analyzed by real-time quantitative PCR (TaqMan® real-time quantitative PCR). The skin panel included normal, non-lesional and lesional psoriatic skin tissue, and lesional and non-lesional atopic dermatitis skin samples. Non-lesional and lesional psoriasis tissue was derived from patient samples with PASI (psoriasis area and severity index) scores between 9-20.75. Non-lesional and lesional atopic dermatitis tissue was derived from patient samples with EASI (eczema area and severity index) scores between 1.85-35.95.

The results of the PCR analysis were normalized to ubiquitin and Kruskal-Wallis statistical analysis was performed on log transformed data (median method). Normal skin tissue samples had an average IL-17A mRNA expression value of 0.42, while the psoriatic non-lesional tissue, psoriatic lesional tissue, non-lesional atopic dermatitis tissue, and lesional atopic dermatitis tissue had average IL-17A expression values of 5.19 (12.3 fold higher), 25.7 (61.2 fold higher), 0.72 (1.7 fold higher) and 2.1 (5 fold higher), respectively, when compared to normal skin, as described in Table 1 (L=Lesional, NL=Nonlesional, AD=Atopic Dermatitis).

TABLE 1

IL-17A Normalized Values

| Normal skin | Psoriasis NL | Psoriasis L | AD NL | AD L |
|---|---|---|---|---|
| 0.13 | 0.08 | 0.06 | 0.12 | 0.11 |
| 4.95 | 16.41 | 55.06 | 0.19 | 0.12 |
| 0.95 | 19.00 | 46.43 | 0.08 | 0.12 |
| 0.09 | 18.13 | 27.84 | 0.07 | 1.53 |
| 0.08 | 0.89 | 13.35 | 0.16 | 0.08 |
| 0.10 | 0.08 | 4.69 | 0.11 | 0.07 |
| 0.06 | 0.66 | 5.53 | 0.09 | 1.31 |
| 0.06 | 2.37 | 10.43 | 0.10 | 0.08 |
| 1.39 | 1.79 | 22.67 | 0.18 | 1.46 |
| 0.07 | 3.84 | 24.76 | 1.55 | 6.00 |
| 0.09 | 6.26 | 51.92 | 1.58 | 0.54 |
| 0.76 | 9.39 | 49.53 | 0.16 | 0.09 |
| 0.06 | 0.09 | 16.50 | 0.53 | 9.01 |
| 1.53 | 0.87 | 22.67 | 1.29 | 2.07 |
| 0.08 | 0.05 | 23.21 | 0.95 | 1.46 |
| 0.11 | 1.02 | 20.51 | 0.09 | 0.53 |
| 0.20 | 0.08 | 11.26 | 0.39 | 3.16 |
| 0.11 | 5.25 | 6.44 | 4.29 | 14.59 |
| 0.09 | 30.77 | 39.85 | 0.07 | 1.29 |
| 0.18 | 1.05 | 9.78 | 0.08 | 0.05 |
| 0.06 |  | 18.34 | 1.07 | 3.62 |
| 0.07 | 0.10 | 41.04 | 0.10 | 0.87 |
| 0.15 | 0.84 | 49.24 | 0.08 | 0.09 |
| 0.10 | 0.75 | 52.22 | 0.16 | 0.11 |
| 1.54 | 4.92 | 19.45 | 1.33 | 2.10 |
| 0.12 |  |  | 0.09 | 1.60 |
| 0.09 |  |  | 0.06 | 0.92 |
| 0.11 |  |  | 2.58 | 5.80 |
| 0.95 |  |  | 0.93 | 2.68 |
| 0.05 |  |  | 3.13 | 1.62 |
| 0.07 |  |  |  |  |
| 0.06 |  |  |  |  |
| 0.05 |  |  |  |  |
| 0.08 |  |  |  |  |
| 0.10 |  |  |  |  |
| Average 0.42 | 5.19 | 25.71 | 0.72 | 2.10 |
| Fold increase over normal |  12.37 | 61.22 | 1.72 | 5.01 |
| Median 0.10 | 1.03 | 22.67 | 0.16 | 1.30 |
| Fold increase over normal | 10.84 | 238.01 | 1.66 | 13.68 |

IL-17F mRNA expression was similarly analyzed. The results of the PCR analysis were normalized to ubiquitin and Kruskal-Wallis statistical analysis was performed on log transformed data (median method). Normal skin tissue samples had an average IL-17F mRNA expression value of 0.90, while the psoriatic non-lesional tissue, psoriatic lesional tissue, non-lesional atopic dermatitis tissue, and lesional atopic dermatitis tissue had average IL-17F expression values of 9.39 (10.43 fold higher), 55.85 (62.05 fold higher), 1.39 (1.54 fold higher) and 4.13 (4.59 fold higher), respectively, when compared to normal skin, as described in Table 2 (L=Lesional, NL=Nonlesional, AD=Atopic Dermatitis).

TABLE 2

IL-17F Normalized Values

| Normal skin | Psoriasis NL | Psoriasis L | AD NL | AD L |
|---|---|---|---|---|
| 0.15 | 0.15 | 1.71 | 0.19 | 1.41 |
| 3.22 | 23.90 | 67.24 | 4.72 | 3.28 |
| 1.49 | 12.30 | 61.57 | 0.09 | 0.18 |
| 0.27 | 33.80 | 64.53 | 1.89 | 3.93 |
| 0.11 | 2.59 | 79.74 | 0.16 | 0.09 |
| 0.11 | 0.13 | 21.50 | 3.13 | 1.19 |
| 1.12 | 0.25 | 20.51 | 0.11 | 0.13 |
| 0.08 | 20.03 | 36.49 | 0.10 | 2.30 |
| 4.22 | 0.09 | 85.06 | 0.24 | 4.80 |
| 0.08 | 0.17 | 44.56 | 0.21 | 11.13 |
| 3.30 | 3.54 | 82.60 | 2.17 | 4.77 |
| 2.64 | 37.14 | 137.74 | 0.17 | 0.09 |
| 0.84 | 0.14 | 27.52 | 2.10 | 7.38 |
| 2.53 | 1.85 | 65.68 | 2.25 | 7.20 |
| 2.58 | 1.35 | 21.62 | 1.79 | 18.24 |
| 0.10 | 0.15 | 22.01 | 0.16 | 1.12 |
| 0.93 | 0.08 | 64.91 | 0.22 | 10.19 |
| 0.31 | 13.43 | 27.20 | 7.33 | 38.92 |
| 0.80 | 50.12 | 68.44 | 0.10 | 0.12 |
| 0.30 | 7.08 | 71.73 | 0.09 | 0.12 |
| 0.13 |  | 86.58 | 1.40 | 1.17 |
| 0.10 | 0.17 | 49.82 | 0.09 | 0.09 |
| 0.22 | 0.12 | 47.54 | 1.29 | 0.12 |
| 0.12 | 5.40 | 106.98 | 0.16 | 1.48 |
| 1.16 | 11.39 | 33.02 | 0.11 | 0.97 |
| 0.13 |  |  | 0.14 | 0.15 |
| 0.10 |  |  | 1.62 | 0.08 |
| 0.14 |  |  | 1.37 | 2.20 |
| 0.77 |  |  | 4.37 | 0.11 |
| 0.16 |  |  | 3.89 | 0.90 |
| 2.83 |  |  |  |  |
| 0.13 |  |  |  |  |
| 0.09 |  |  |  |  |
| 0.09 |  |  |  |  |
| 0.13 |  |  |  |  |
| Average 0.90 | 9.39 | 55.85 | 1.39 | 4.13 |
| Fold increase over normal |  10.43 | 62.05 | 1.54 | 4.59 |
| Median 0.22 | 2.22 | 61.57 | 0.23 | 1.18 |
| Fold increase over normal | 10.19 | 282.24 | 1.04 | 5.40 |

IL19 mRNA expression was also analyzed. The results of the PCR analysis were normalized to ubiquitin and Kruskal-Wallis statistical analysis was performed on log transformed data (median method). Normal skin tissue samples had an average IL-19 mRNA expression value of 0.75, while the psoriatic non-lesional tissue, psoriatic lesional tissue non-lesional atopic dermatitis tissue, and lesional atopic dermatitis tissue had average IL-19 expression values of 23.44 (31.11 fold higher), 199.40 (264.66 fold higher), 9.65 (12.80 fold higher) and 31.55 (41.88 fold higher), respectively, when compared to normal skin, as described in Table 3 (L=Lesional, NL=Nonlesional, AD=Atopic Dermatitis).

TABLE 3

IL-19 Normalized Values

| Normal skin | Psoriasis NL | Psoriasis L | AD NL | AD L |
|---|---|---|---|---|
| 0.13 | 3.13 | 15.47 | 1.16 | 5.60 |
| 19.68 | 65.68 | 192.56 | 0.19 | 0.12 |
| 1.80 | 40.09 | 126.86 | 0.08 | 1.58 |
| 0.09 | 66.45 | 133.75 | 0.72 | 2.01 |
| 0.08 | 2.28 | 44.30 | 0.16 | 2.90 |
| 0.10 | 0.84 | 63.78 | 0.11 | 1.09 |
| 0.06 | 0.06 | 9.17 | 0.09 | 0.07 |
| 0.06 | 8.25 | 30.23 | 0.10 | 0.08 |
| 0.06 | 2.70 | 588.28 | 2.97 | 11.87 |
| 0.07 | 14.16 | 41.77 | 0.49 | 13.04 |
| 1.02 | 13.75 | 784.64 | 71.73 | 348.65 |
| 0.10 | 40.56 | 212.80 | 8.85 | 14.50 |
| 0.06 | 4.15 | 92.36 | 6.95 | 20.51 |
| 0.14 | 17.40 | 143.53 | 123.19 | 282.16 |
| 0.08 | 10.56 | 97.95 | 0.16 | 0.91 |
| 0.11 | 5.66 | 39.15 | 4.83 | 6.48 |
| 0.20 | 0.99 | 116.84 | 0.39 | 1.36 |
| 0.11 | 11.46 | 4.48 | 9.44 | 25.80 |

TABLE 3-continued

IL-19 Normalized Values

| Normal skin | Psoriasis NL | Psoriasis L | AD NL | AD L |
|---|---|---|---|---|
| 0.09 | 163.34 | 171.20 | 3.75 | 4.53 |
| 0.18 | 14.76 | 63.78 | 0.08 | 0.05 |
| 0.06 | 1.53 | 129.88 | 7.38 | 24.32 |
| 0.07 | 0.07 | 856.96 | 2.36 | 4.64 |
| 0.15 | 7.46 | 473.30 | 0.08 | 8.30 |
| 0.10 | 67.24 | 354.86 | 0.63 | 27.84 |
| 0.07 | | 197.14 | 4.61 | 4.48 |
| 0.12 | | | 0.98 | 0.12 |
| 0.09 | | | 0.06 | 0.69 |
| 0.11 | | | 1.85 | 13.20 |
| 0.07 | | | 3.38 | 6.83 |
| 0.05 | | | 32.63 | 112.79 |
| 0.07 | | | | |
| 0.06 | | | | |
| 0.05 | | | | |
| 0.97 | | | | |
| 0.10 | | | | |
| Average 0.75 | 23.44 | 199.40 | 6.65 | 31.55 |
| Fold increase over normal | 31.11 | 264.66 | 12.80 | 41.88 |
| Median 0.09 | 9.40 | 126.86 | 1.07 | 5.12 |
| Fold increase over normal | 99.31 | 1339.95 | 11.27 | 54.03 |

IL-17A, first isolated from an activated rodent T-cell hybridoma, was initially named CTLA-8 (see, e.g., Rouvier, et al. (1993) *J. Immunol.* 150:5445-5456). The cytokine had substantial homology (58%) to an open-reading frame in *Herpesvirus samiri*. Initial biological characterization found that IL-17 could promote the production of other inflammatory cytokines and chemokines such as IL-6, IL-8, and G-CSF from epithelial, endothelial, and fibroblast cells (see, e.g., Yao, et al. (1995) *Immunity* 3:811-821; Kennedy, et al. (1996) *J. Interferon Cytokine Res.* 16:611-617; and Fossiez, et al. (1996) *J. Exp. Med.* 183:2593-2603). IL-17 has been associated in various inflammatory and proliferative disorders, including rheumatoid arthritis, airway inflammation, transplant rejection, systemic sclerosis, psoriasis, and tumor growth (see, e.g., Aggarwal and Gurney (2002) *J. Leukocyte Biology* 71:1-8).

IL-17F has high sequence identity to IL-17A. However, the level of expression of IL-17F (also known as ML-1) is low compared to that of IL-17A and the expression patterns for IL-17F are quite distinct from those of IL-17A. RT-PCR results indicate that IL-17F is expressed by activated CD4+T cells and activated monocytes (see, e.g., Starnes, et al. (2001) *J. Immunol.* 167:4137-4140). IL-17F expression and activity has been linked to pulmonary epithelial cells as well angiogenesis (see, e.g., Starnes, et al. supra; Kawaguchi, et al. (2001) *J. Immunol.* 167:4430-4435; and Kawaguchi, et al. (2004) *J. Allergy Clin. Immunol.* 114:1265-1273). The present invention reveals that expression of IL-17F in lesional and non-lesional psoriasis and atopic dermatitis mirrors the expression of IL-17A in the same tissues (see, e.g., Tables 1 and 2). Thus, using one or both of the IL-17 family member expression levels should provide useful information in predicting the outbreak of these two inflammatory skin disorders. Also antagonizing one or both of these cytokines should provide preventative therapy to avoid outbreaks of these disorders.

IL-19 is a member of a novel family of IL-10-related cytokines that consists of IL-19, IL-20, and IL-24. Monocytes are the major hematopoietic source of IL-19 (Nagalakshmi et al, (2004) *Int Immunopharmacol* 4:577-592). Monocytes also respond to IL-19 by producing IL-6 and TNF (Liao et al, (2002) *J Immunol* 169:4288-4297). IL-19 binds to the heterodimeric receptor IL-20R1/IL-20R2 (Parrish-Novak (2002), *J. Biol Chem* 277: 47517-47523). These receptor subunits are highly expressed in epithelial cells, including keratinocytes (Wang et al (2002) *J Biol Chem* 277:7341-7347; Blumberg et al. (2001) *Cell* 104:9-19), and are elevated in human psoriatic skin (Romer et al (2003) *J Invest Dermatol* 6:1306-1311), suggesting a possible role in psoriasis pathogenesis. IL-19 mRNA is expressed by keratinocytes in human psoriatic lesions and disappears after treatment with cyclosporin or calcipotriol (Romer et al, supra). IL-19 mRNA is also reduced in psoriatic patients after IL-4 therapy (Ghoreschi et al (2003) *Nat Med* 9:40-46). Elevated IL-19 levels in serum has also been associated with asthma (Liao et al (2004) *J Immunol.* 173:6712-6718).

IL-23 is a heterodimeric cytokine composed of one unique subunit, p19 (also known as IL-B30, IL-30) in association with the p40 subunit from IL-12 (see, e.g., Oppmann, et al. (2000) *Immunity* 13:715-725). Transgenic overexpression of IL-23p19 was shown to be sufficient for the induction of systemic inflammation and premature death, however, this effect appeared to be IFNγ-independent. Thus, suggesting that IL-23 has effects independent and substantially different from IL-12 (see, e.g., Wiekowski, et al. (2001) *J. Immunol.* 166:7563-7570). Recent studies have shown that IL-23 may act to induce a distinct T cell activation state leading to the production of IL-17 (see, Aggarwal, et al. (2003) *J. Biol. Chem.* 278:1910-1914). Therefore, antagonizing IL-17 and/or IL-23 should be efficatious in the prevention of cutaneous inflammation, in particular, psoriasis.

IL-23 gene expression is increased in human psoriasis (Lee et al, (2004) *J Exp Med* 199:125-130). To investigate whether IL-23 may play a role in disease pathogenesis, we injected 1 µg IL-23 intradermally daily into three different wild-type mouse strains (C57Bl/6, 129SvEv, and B6×129) and examined its effect on skin histologically and by gene expression. IL-23 induced clinical and histological changes in mouse skin that bears some similarities to human psoriatic lesions, Table 4.

TABLE 4

Comparison of clinical and histological features of human psoriasis with IL-23-treated mouse skin.

| | Human psoriasis | IL-23-treated wild-type skin |
|---|---|---|
| Clinical | | |
| Erythematous | yes | yes |
| Well-demarcated from symptomless skin | yes | no |
| White silvery scale | yes | no, although small areas of flaky skin |
| Histological | | |
| Acanthosis | yes | yes |
| Parakeratosis | yes | yes |
| Elongation of rete ridges | yes | no |
| Intracorneal pustules (Munro microabscesses) | yes | yes |
| Recruitment to dermis of- | | |
| CD4+ lymphocytes | yes | yes |
| dendritic cells | yes | yes |
| macrophages | yes | yes |
| neutrophils | yes | yes |
| mast cells | yes | no |
| CD8+ cells in epidermis | yes | no |

TABLE 4-continued

Comparison of clinical and histological features of human psoriasis with IL-23-treated mouse skin.

|  | Human psoriasis | IL-23-treated wild-type skin |
|---|---|---|
| Prominent dermal papillary blood vessels | yes | yes |

IL-23 induced the expression of IL-17, IL-17F, and IL-19 in comparison to vehicle control suggesting that these cytokines may form part of an important pathway whose dysregulation may contribute to psoriasis pathogenesis, Table 5. Antagonism of either of these cytokines may therefore be efficacious in the treatment of cutaneous inflammatory diseases such as psoriasis.

TABLE 5

IL-23 induces IL-17A, IL-17F, and IL-19 gene expression in mice. Values are relative to ubiquitin and represent pooled mRNA (n = 4) from three different wild-type strains.

| | Vehicle | Avg. | IL-23 | Avg |
|---|---|---|---|---|
| | | | Day 1 | |
| IL-17A | 1.42, 9.43, 0.07 | 3.64 | 47.86, 48.71, 18.62 | 38.40 |
| IL-17F | 1.2, 1.02, 0.05 | 0.76 | 184.73, 91.21, 66.72 | 114.22 |
| IL-19 | 0.89, 3.16, 0.96 | 1.67 | 12.9, 16.07, 10.04 | 13.00 |
| | | | Day 4 | |
| IL-17A | 2.76, 5.81, 0.23 | 2.93 | 23.36, 44.19, 4.27 | 23.94 |
| IL-17F | 5.53, 1.93, 0.06 | 2.51 | 43.24, 38.10, 22.76 | 34.70 |
| IL-19 | 0.97, 2.82, 4.89 | 2.89 | 56.51, 58.22, 109.36 | 74.70 |

III. Binding Compositions.

Binding compositions provided by the methods of the present invention include reagents such as IL-17, IL-19, and IL-23, soluble receptors, and antibodies, as well as nucleic acids encoding these reagents.

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378; Baca, et al. (1997) *J. Biol. Chem.* 272:10678-10684; Chothia, et al. (1989) *Nature* 342:877-883; Foote and Winter (1992) *J. Mol. Biol.* 224:487-499; U.S. Pat. No. 6,329,511 issued to Vasquez, et al.).

An alternative to humanization is to use human antibody libraries displayed on phage or human antibody libraries in transgenic mice (Vaughan, et al. (1996) *Nature Biotechnol.* 14:309-314; Barbas (1995) *Nature Medicine* 1:837-839; Mendez, et al. (1997) *Nature Genetics* 15:146-156; Hoogenboom and Chames (2000) *Immunol. Today* 21:371-377; Barbas, et al. (2001) *Phage Display:A Laboratory Manual*, Cold Spring Harbor Laboratory Press, Cold Spring Harbor, N.Y.; Kay, et al. (1996) *Phage Display of Peptides and Proteins:A Laboratory Manual*, Academic Press, San Diego, Calif.; de Bruin, et al. (1999) *Nature Biotechnol.* 17:397-399).

Single chain antibodies and diabodies are described (see, e.g., Malecki, et al. (2002) *Proc. Natl. Acad. Sci. USA* 99:213-218; Conrath, et al. (2001) *J. Biol. Chem.* 276:7346-7350; Desmyter, et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248: 7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

The present invention provides a bispecific antibody that can bind specifically to at least two cytokines chosen from IL-17, IL-19, or IL-23, or receptors, thereof. (see, e.g., Azzoni, et al. (1998) *J. Immunol.* 161:3493; Kita, et al. (1999) *J. Immunol.* 162:6901; Merchant, et al. (2000) *J. Biol. Chem.* 74:9115; Pandey, et al. (2000) *J. Biol. Chem.* 275:38633; Zheng, et al. (2001) *J. Biol Chem.* 276:12999; Propst, et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard, et al. (1997) *Immunity* 7:283-290; Wright, et al. (2000) *Immunity* 13:233-242; Preston, et al., supra; Kaithamana, et al. (1999) *J. Immunol.* 163:5157-5164).

Antibodies will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) *Thromb. Haemost.* 85:379-389; Yang, et al. (2001) *Crit. Rev. Oncol. Hematol.* 38:17-23; Carnahan, et al. (2003) *Clin. Cancer Res. (Suppl.)* 9:3982s-3990s).

Polypeptides, antibodies, and nucleic acids, can be conjugated, e.g., to small drug molecules, enzymes, liposomes, polyethylene glycol (PEG), or fusion protein antibodies. Antibodies are useful for diagnostic or kit purposes, and include antibodies coupled, e.g., to dyes, radioisotopes, enzymes, or metals, e.g., colloidal gold (see, e.g., Le Doussal, et al. (1991) *J. Immunol.* 146:169-175; Gibellini, et al. (1998) *J. Immunol.* 160:3891-3898; Hsing and Bishop (1999) *J. Immunol.* 162:2804-2811; Everts, et al. (2002) *J. Immunol.* 168:883-889).

The invention also provides binding compositions for use as anti-sense nucleic acids or for small interference RNA (siRNA) (see, e.g., Arenz and Schepers (2003) *Naturwissenschaften* 90:345-359; Sazani and Kole (2003) *J. Clin. Invest.* 112:481-486; Pirollo, et al. (2003) *Pharmacol. Therapeutics* 99:55-77; Wang, et al. (2003) *Antisense Nucl. Acid Drug Devel.* 13:169-189; Cheng, et al. (2003) *Mol. Genet. Metab.* 80:121-128; Kittler and Buchholz (2003) *Semin. Cancer Biol.* 13:259-265).

IV. Purification and Modification of Polypeptides and Nucleic Acids.

Polypeptides, e.g., antigens, antibodies, and antibody fragments, and nucleic acids for use in the contemplated method, can be purified by methods that are established in the art. Purification can involve homogenization of cells or tissues, immunoprecipitation, and chromatography. Stability during purification or storage can be enhanced, e.g., by anti-protease agents, anti-oxidants, ionic and non-ionic detergents, and solvents, such as glycerol or dimethylsulfoxide.

Modification of, e.g., peptides, polypeptides, and nucleic acids, includes epitope tags, fluorescent or radioactive groups, monosaccharides or oligosaccharides, sulfate or phosphate groups, C-terminal amides, acetylated and esterified N-groups, acylation, e.g., fatty acid, intrachain cleaved peptide bonds, and deamidation products (see, e.g., Johnson, et al. (1989) *J. Biol. Chem.* 264:14262-14271; Young, et al. (2001) *J. Biol. Chem.* 276:37161-37165). Glycosylation depends upon the nature of the recombinant host organism employed or physiological state (see, e.g., Jefferis (2001) *BioPharm* 14:19-27; Mimura, et al. (2001) *J. Biol. Chem.* 276:45539-45547; Axford (1999) *Biochim. Biophys. Acta* 1:219-229; Malhotra, et al. (1995) *Nature Medicine* 1:237-243).

V. Therapeutic Compositions and Methods.

To prepare pharmaceutical or sterile compositions including an antagonist of IL-17 or IL-23, the reagents is mixed with a pharmaceutically acceptable carrier or excipient. Formulations of therapeutic, prophylactic, and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Selecting an administration regimen for a prophylactic or therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg body weight basis. The desired plasma concentration of a small molecule therapeutic is about the same as for an antibody, on a moles/kg body weight basis.

An effective amount for a particular patient may vary depending on factors such as the condition being treated, the overall health of the patient, the method route and dose of administration and the severity of side affects, see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, $10^{th}$ ed., McGraw-Hill, New York, N.Y.; Poole and Peterson (eds.) (2001) *Pharmacotherapeutics for Advanced Practice:A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa.). An effective amount of therapeutic will decrease the symptoms typically by at least 10%; usually by at least 20%; preferably at least about 30%; more preferably at least 40%, and most preferably by at least 50%.

The route of administration is by, e.g., topical or cutaneous application, injection or infusion by intravenous, intraperitoneal, intracerebral, intramuscular, intraocular, intraarterial, intracerebrospinal, intralesional, or pulmonary routes, or by sustained release systems or an implant (see, e.g., Sidman et al. (1983) *Biopolymers* 22:547-556; Langer, et al. (1981) *J. Biomed. Mater. Res.* 15:167-277; Langer (1982) *Chem. Tech.* 12:98-105; Epstein, et al. (1985) *Proc. Natl. Acad. Sci. USA* 82:3688-3692; Hwang, et al. (1980) *Proc. Natl. Acad. Sci. USA* 77:4030-4034; U.S. Pat. Nos. 6,350,466 and 6,316,024).

VI. Kits.

The present invention diagnostic kits/ Provided are binding compositions, including antibodies or antibody fragments, for the detection of IL-17, IL-19, or IL-23, and metabolites and breakdown products thereof, including products resulting from deamidation, limited proteolytic or hydrolytic cleavage, or disulfide bond oxidation or formation. Typically, the kit will have a compartment containing either a IL-17, IL-19, or IL-23 polypeptide, or an antigenic fragment thereof, a binding composition thereto, or a nucleic acid, e.g., a nucleic acid probe or primer, able to hybridize under stringent conditions to a nucleic acid encoding IL-17, IL-19, or IL-23.

The kit can comprise, e.g., a reagent and a compartment, a reagent and instructions for use, or a reagent with a compartment and instructions for use. The reagent can comprise full length IL-17, IL-19, or IL-23 polypeptide, or an antigenic fragment thereof, a binding composition, or a nucleic acid. A kit for determining the binding of a test compound, e.g., acquired from a biological sample or from a chemical library, can comprise a control compound, a labeled compound, and a method for separating free labeled compound from bound labeled compound.

Conditions enabling stringent hybridization of nucleic acid probes or primers are available (see, e.g., Freeman, et al. (2000) *Biotechniques* 29:1042-1055; de Silva and Wittwer (2000) *J. Chromatogr. B. Biomed. Sci. Appl.* 741:3-13; Long (1998) *Eur. J. Histochem.* 42:101-109; Musiani, et al. (1998) *Histol. Histopathol.* 13:243-248; Gillespie (1990) *Vet. Microbiol.* 24:217-233; Giulietti, et al. (2001) *Methods* 25:386-401; Schweitzer and Kingsmore (2001) *Curr. Opin. Biotechnol.* 12:21-27; Speel, et al. (1999) *J. Histochem. Cytochem.* 47:281-288; Tsuruoka and Karube (2003) *Comb. Chem. High Throughput Screen.* 6:225-234; Rose, et al. (2002) *Biotechniques* 33:54-56).

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals (see, e.g., Le Doussal, et al. (1991) *New Engl. J. Med.* 146:169-175; Gibellini, et al. (1998) *J. Immunol.* 160:3891-3898; Hsing and Bishop (1999) *New Engl. J. Med.* 162:2804-2811; Everts, et al. (2002) *New Engl. J. Med.* 168:883-889). Various assay formats exist, such as Real-time PCR, radioimmunoassays (RIA), ELISA, and lab on a chip (U.S. Pat. Nos. 6,176,962 and 6,517,234).

The diagnostic method can comprise contacting a sample from a test subject with a binding composition that specifically binds to a polypeptide or nucleic acid of IL-17, IL-19, or IL-23. Moreover, the diagnostic method can further comprise contacting the binding composition to a sample derived from a control subject or control sample, and comparing the binding found with the test subject with the binding found with the control subject or control sample. A "test sample" can be derived from a skin sample from a subject experiencing psoriasis, both lesional and non-lesional, while a "control sample" can be derived from a skin sample from a normal subject, or derived from a non-affected skin sample from the subject experiencing cutaneous inflammation. The subject can be, e.g., human, veterinary, experimental, or agricultural. Derived encompasses a biopsy, sample, extract, or a processed, purified, or semi-purified sample or extract.

Alternatively, both test and normal skin samples, as defined above, can be obtained and subjected to standard mRNA extraction protocols. The mRNA is subsequently reversed transcribed into ssDNA, which is then used for a second DNA strand synthesis. The double strand DNA is then used in real-time PCR, e.g., TaqMan® real-time Quantitative PCR, reactions. Data are analyzed as described below.

VII. Uses.

The invention provides methods for the diagnosis or prevention of cutaneous inflammation, including but not limited to, cicatricial pemphigoid, scleroderma, hidradenitis suppurativa, toxic epidermal necrolysis, acne, osteitis, graft vs. host disease (GvHD), pyoderma gangrenosum, and Behcet's Syndrome (see, e.g., Willams and Griffiths (2002), supra). The most common form of cutaneous inflammation is psoriasis.

The broad scope of this invention is best understood with reference to the following examples, which are not intended to limit the inventions to the specific embodiments.

EXAMPLES

I. General Methods.

Methods for the diagnosis, prevention, and treatment of inflammatory conditions of the skin in animals and humans are described (see, e.g., Ackerman (1997) *Histological Diagnosis of Inflammatory Skin Disease*, $2^{nd}$ ed., Lippincott, Williams, and Wilkins, New York, N.Y.; Gallin, et al. (1999) *Inflammation:Basic Principles and Clinical Correlates*, $3^{rd}$ ed., Lippincott, Williams, and Wilkins, New York, N.Y.; Parnham, et al. (1991) *Drugs in Inflammation (Agents and Actions Suppl.*, Vol. 32), Springer Verlag, Inc., New York, N.Y.; Chan (ed.) (2003) *Animal Models of Human Inflammatory Skin Diseases*, CRC Press, Boca Raton, Fla.; Kownatzki and Norgauer (eds.) (1998) *Chemokines and Skin*, Birkhauser Verlag, Basel, Switzerland; Kanitakis, et al. (eds.) (1999) *Diagnostic Immunohistochemistry of the Skin,* Lippincott, Williams, and Wilkins, New York, N.Y.).

Animal models of cutaneous inflammation, and related methods, are available. These methods include use of skin grafts, skin grafts injected with immune cells, subcutaneous injection of immune cells, and use of animals such as various mouse models of psoriasis, in particular xenotransplatation models (see, e.g., Kruger, et al. (1981) *J. Clin. Invest.*, 68:1548-1577; Nickoloff, et al. (1995) *Am. J. Pathol.* 146:580-588; and Schön (1999) *J. Invest. Dermatol.* 112:405-410).

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies is described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protcols in Immunology*, Vol. 4, John Wiley, Inc., New York).

Standard techniques in cell and tissue culture are described (see, e.g., Freshney (2000) *Culture of Animal Cells: A Manual of Basic Technique*, $4^{th}$ ed., Wiley-Liss, Hoboken, N.J.; Masters (ed.) (2000) Animal Cell Culture: A Practical Approach, $3^{rd}$ ed., Oxford Univ. Press, Oxford, UK; Doyle, et al. (eds.) (1994) *Cell and Tissue Culture: Laboratory Procedures*, John Wiley and Sons, NY; Melamed, et al. (1990) *Flow Cytometry and Sorting* Wiley-Liss, Inc., New York, N.Y.; Shapiro (1988) Practical Flow Cytometry Liss, New York, N.Y.; Robinson, et al. (1 993) *Handbook of Flow Cytometry Methods,* Wiley-Liss, New York, N.Y.).

Software packages for determining, e.g., antigenic fragments, signal and leader sequences, protein folding, and functional domains, are available. See, e.g., Vector NTI® Suite (Informax, Inc., Bethesda, Md.); GCG Wisconsin Package (Accelrys, Inc., San Diego, Calif.), and DeCypher® (Time-Logic Corp., Crystal Bay, Nev.); Menne, et al. (2000) *Bioinformatics* 16:741-742. Public sequence databases were also used, e.g., from GenBank and others.

II. Real-time PCR

Total RNA from homogenized tissue samples (see below) was extracted and reverse transcribed as previously described (see, e.g., Homey, et al. (2000) *J. Immunol.* 164:3465-3470). Complementary DNA was quantitatively analyzed for expression of IL-17 by the fluorgenic 5'-nuclease PCR assay (see, e.g., Holland, et al. (1991) *Proc. Natl. Acad. Sci.* 88:7276-7280). Specific primers used were as follows:

```
Human IL-17A Forward Primer
5'-CAACCGATCCACCTCACCTT-3'        SEQ ID NO:1

Human IL-17A Reverse Primer
5'-GGCACTTTGCCTCCCAGAT-3'         SEQ ID NO:2

Human IL-17F Forward Primer:
5'-TGCCAGGAGGTAGTATGAAGCTT-3'     SEQ ID NO:3

Human IL-17F Reverse Primer:
5'-ATGCAGCCCAAGTTCCTACACT-3'      SEQ ID NO:4

Human IL-19 Forward Primer:
5'-TTGGCTCCTGGGTACAATACTG-3'      SEQ ID NO:5

Human IL-19 Reverse Primer:
5'-TCCTTAGCTTGGATGGCTCTTT-3'      SEQ ID NO:6
```

IL-17 or IL-19 specific PCR products were continuously measured by means of an ABI PRISM 7700 Sequence Detection System (Applied Biosystems) during 40 cycles. Values were normalized to ubiquitin. Log-transformed data was subjected to Kruskal-Wallis statistical analysis (median method). The expression level (log transformed) corresponds to the amount of IL-17 or IL-19 expressed in the tissue sample, such that the higher the expression level (log transformed), the greater the amount of IL-17 or IL-19 expressed in the tissue sample.

III. Human Inflammatory Skin Disease Panel

The human inflammatory skin disease panel included normal skin, non-lesional and lesional skin from psoriatic and atopic dermatitis patients. The panel included 35 normal skin samples (15 from autopsy donors and 20 from normal donors in clinical trial setting, see below), 24 non-lesional psoriasis skin samples, 25 lesional psoriasis skin samples, 30 non-lesional atopic dermatitis skin samples, and 30 lesional atopic dermatitis skin samples. Two 4mm punch biopsies were taken from each patient. Non-lesional psoriatic and atopic dermatitis skin samples were taken from sites distal to a psoriatic or atopic dermatitis lesion. Samples were obtained in a clinical trial setting at Stanford University Dermatology Department. Autopsy donor materials were obtained from Zoion. The study was approved by the local ethics committees of the respective institutions.

All non-lesional and lesional patient samples were ranked by severity using either the PASI (psoriasis area and severity index) score or EASI (eczema area and severity index) score. For psoriasis patients, the PASI scores were in the range of 9-20.75. For atopic dermatitis patients, the EASI scores were in the range of 1.85-35.95. These scores reflected the extent and severity of disease over the patient's body.

IV. Methods for Cell Culture, Histology, and Skin Grafting.

Alternatively, cell lines may be used. Cell lines are cultured in Dulbecco's modified Eagle medium (DMEM) (GIBCO BRL, Grand Island, N.Y.) supplemented with 10% fetal bovine serum (FBS). Human keratinocytes may be derived from newborn human foreskins and are cultured in Keratinocyte SFM (GIBCO BRL; Rheinwald and Green (1975) *Cell* 6:317-330). Skin is separated by gently tearing along the cartilage plate and floated on 0.5% trypsin (GIBCO BRL) in phosphate buffered saline (PBS) at 37° C. for 45 min. Epidermal sheets are peeled from the dermis, re-suspended in 0.05% DNAase (Sigma, St. Louis, Mo.) in PBS containing 10% fetal bovine serum (FBS). Single cell suspension is obtained by vigorous passage through a syringe. For reverse transcription polymerase chain reaction (RT-PCR) analysis, cells are cultured in Keratinocyte SFM, and RNA is isolated by standard methodologies.

For flow cytometry, freshly isolated epidermal cells are washed once in cold phosphate buffered saline (PBS) and $4 \times 10^5$ cells are stained for 30 min at 4° C. with any of the appropriately labeled antibody reagents. Cells are washed twice in cold PBS and analyzed by flow cytometry on a Becton Dickenson FACScan® flow cytometer (San Jose, Calif.).

Many modifications and variations of this invention, as will be apparent to one of ordinary skill in the art, can be made to adapt to a particular situation, material, composition of matter, process, process step or steps, to preserve the objective, spirit, and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of the equivalents to which such claims are entitled; and the invention is not to be limited by the specific embodiments that have been presented herein by way of example.

What is claimed is:

1. A method of evaluating the propensity of a subject to develop an inflammatory skin disorder comprising:
   a) obtaining a non-lesional skin sample from the subject;
   b) quantifying the level of IL-17A, IL-17F or IL-19 expression in the skin sample; and
   c) comparing the level of IL-17A, IL-17F or IL-19 in the skin sample to the level in normal skin samples, wherein higher levels of expression of IL-17A, IL-17F or IL-19 than normal skin indicate a propensity of the subject to develop an inflammatory skin disorder.

2. The method of claim 1, wherein the IL-17A, IL-17F or IL-19 expression is mRNA expression.

3. The method of claim 1, wherein the level of IL-17A, IL-17F or IL-19 expression is quantified by real-time PCR.

4. The method of claim 1, wherein the inflammatory skin disorder is cutaneous inflammation.

5. The method of claim 4, wherein the cutaneous inflammation is psoriasis.

6. The method of claim 1, wherein the level of IL-17A or IL-17F expression in the skin sample is at least 5-fold higher than normal skin.

7. The method of claim 1, wherein the level of IL-19 expression in the skin sample is at least 20-fold higher than normal skin.

8. The method of claim 1, wherein the subject has:
a) a family history of psoriasis; or
b) previously presented psoriatic symptoms.

9. The method of claim 1, wherein the subject is a human.

10. The method of claim 1, wherein the level of IL-17A or IL-17F expression in the skin sample is 2 to 50 fold higher than normal skin.

11. The method of claim 10, wherein the level of IL-17A or IL-17F expression in the skin sample is 5 to 20 fold higher than normal skin.

12. The method of claim 1, wherein the level of IL-19 expression in the skin sample is 5 to 130 fold higher than normal skin.

* * * * *